United States Patent [19]

Okumura et al.

[11] Patent Number: 4,737,587
[45] Date of Patent: Apr. 12, 1988

[54] COLORLESS CARBAZOLE DYES FOR RECORDING MATERIALS

[75] Inventors: Fumio Okumura, Takasago; Hirokazu Tsukahara; Haruhiko Ikeda, both of Tokyo, all of Japan

[73] Assignee: Mitsubishi Paper Mills, Ltd., Tokyo, Japan

[21] Appl. No.: 932,944

[22] Filed: Nov. 20, 1986

[30] Foreign Application Priority Data

Nov. 25, 1985 [JP] Japan .................................. 60-265749
Nov. 28, 1985 [JP] Japan .................................. 60-268740
Dec. 2, 1985 [JP] Japan .................................. 60-269392

[51] Int. Cl.$^4$ .......................................... C07D 209/86
[52] U.S. Cl. ................................. 548/444; 427/151; 503/223; 503/224
[58] Field of Search ....................................... 548/444

[56] References Cited

U.S. PATENT DOCUMENTS 4,275,005  6/1981  Petitpierre et al. ................ 548/444

Primary Examiner—Robert W. Ramsuer
Attorney, Agent, or Firm—Cushman, Darby & Cushman

[57] ABSTRACT

Disclosed is a colorless dye for use in recording materials comprising a compound represented by the general formula:

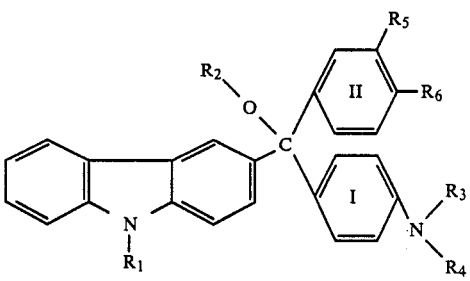

Said recording materials are of the types which utilize a color developing reaction between an electron-donating colorless dye and an electron-accepting color developer, such as, carbonless pressure-sensitive recording materials, thermosensitive recording materials, etc.

5 Claims, No Drawings

COLORLESS CARBAZOLE DYES FOR RECORDING MATERIALS

BACKGROUND OF THE INVENTION

This invention relates to a novel colorless dye (precursor) suitable for use in image recording materials which utilize a color developing reaction between an electron-donating colorless dye and an electron-accepting color developer, such as, for example, carbonless pressure-sensitive recording materials, thermosensitive recording materials, and other image recording materials.

As the colorless dyes used heretobefore for the above-mentioned purpose, there may be mentioned so-called lactone dyes including colorless dye of the triphenylmethane lactone type such as typically 3,3-bis(4-dimethylaminophenyl-6-dimethylaminophthalide (so-called Crystal Violet Lactone) and those of the fluorane lactone type such as typically 3-diethylamino-6-methyl-7-anilinofluorane. These lactone dyes are well-known as primary dyes (colorless dyes capable of developing colors immediately upon contact with acid substances which act as color developers).

On the other hand, dyes in reduced form and acylated derivatives thereof such as benzoyl-leucoMethylene Blue and carbazolylmethane compounds described in Japanese Patent Publication No. 16,358/85 can also be used as colorless dye. These dyes, however, do not form color unless brought into contact with developers of high oxidizing power (inorganic solid acids such as acid clays or activated clays are usually used). Moreover, even when the contact is made, an extended period of time is required before color is slowly developed (such colorless dyes are called secondary dyes). The secondary dyes do not form colors with the well-known developers based on organic acid substances such as phenolic compounds or polyvalent metal salts of salicylic acid.

Crystal Violet Lactone has been generally used as a primary dye, especially as that which gives blue-colored images. The color image formed from Crystal Violet lactone is susceptible to fading, especially fading caused by light or a plasticizer. As a consequence, there has been a strong request for the improvement in color fastness of primary dyes.

The colorless dye provided by the present invention are a group of novel compounds not described in the literature.

As described above, there has been known no colorless dye to be used as a primary dye capable of forming an image in fast blue color by momentarily reacting with various common developers (acid substances).

SUMMARY OF THE INVENTION

Therefore, an object of this invention is to provide a colorless primary dye for use in image recording materials comprising a tri-(amino-substituted aryl)-di-alkoxyarylcarbinol, or an ether derivative of these carbinols, said compounds necessarily having a carbazole ring and being different chemically (in structure and reaction mechanism) from the lactone dyes.

Another specific object of this invention is to provide a colorless dye capable of reacting with a wide variety of developers (acid substances) to form a fast-colored image, the acid sensibility being moderate enough to keep the image recording material from discoloration or staining (i.e. fogging).

DETAILED DESCRIPTION OF THE INVENTION

Regarding the tri-(amino-substituted aryl)carbinols or ether derivatives thereof, there is described in "Beilsteins Handbuck der Organischen Chemie", Vol. 13, p. 755 or 758 a carbinol base of Crystal Violet or an ether derivative thereof such as 4,4',4''-tris(dimethylamiotriphenyl)carbinol or an ether derivative thereof, which is easily decomposed by an acid such as, for example, carbonic acid.

According to the experimental results obtained by the present inventors, such a carbinol or an ether derivative is excessively sensitive to acids and so a blue color is developed even when contacted, for example, with the fingers or an ordinary paper sheet. In another experiment, if the microencapsulation of such a compound is attempted for the purpose of using the compound in a carbonless pressure-sensitive recording material, then a color is developed too early in the process of microencapsulation. If the compound is mixed with crystals of bisphenol A for the purpose of using the compound in a thermosensitive recording sheet, then a color is developed even at room temperature. Thus the compound was found useless for the practical purpose of using it as a colorless dye in image recording materials.

On the other hand, Japanese Patent Application "Kokai" (Laid-open) No. 76,317/79 proposes a triarylcarbinol or an ether derivative thereof comprising one aryl group having no amino group and two aryl groups which may have nitrogen atoms. The experiment conducted by the present inventor revealed that a triarylcarbinol or an ether derivative thereof having even one aryl group bearing no amino substituent group forms an image of very pale color when contacted with a developer (acid substance) and is unsuitable for the practical purposes.

For the purpose of finding out a triarylcarbinol or an ether derivative thereof which will not discolor or stain the image recording material and is still capable of reacting with a wide variety of developers to form an image record of high density, the present inventors accumulated experimental data on the synthesis and testing of desirable chemical structure of the three aryl groups. As a result, it was discovered that fogging becomes distinct if even one of the three aryl groups is N,N-dialkylaminophenyl group and that a high-density recorded image is obtained if all of the three aryl groups are nitrogen-containing aromatic amine groups. It was also discovered that an image record of higher density is obtained without causing discoloration or staining of the recording material when said aromatic amine group is a hetero ring containing a nitrogen atom in the ring, preferably a carbazole ring, and the number of such hetero rings is greater and also that an image record of high density is obtained with little discoloration or staining when one of the three carbazole rings is a benzene ring having two ether substituents. The above discoveries have led to the present invention.

The novel colorless dyes provided by the present invention are a group of compounds represented by the general formula (I):

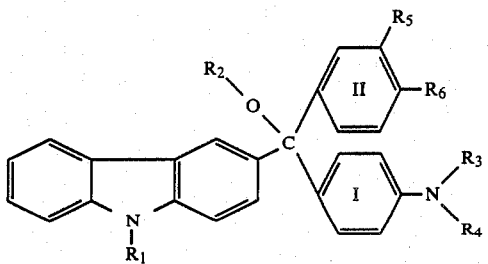 (I)

wherein $R_1$, $R_2$ and $R_3$ represent each a hydrogen atom or a straight-chain, branched-chain or cyclic alkyl or alkenyl grop or an aralkyl group which may have a substituent group; $R_4$ represents an alkyl or aromatic ring group which may have a substituent group (said aromatic ring group may be jointed to the ring I and form together with the nitrogen atom a heterocyclic group; $R_5$ and $R_6$ both represent $OR_7$ (where $R_7$ represents a hydrogen atom or an alkyl, alkenyl or aralkyl group); or $R_5$ represents a hydrogen atom and $R_6$ represents

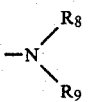

[where $R_8$ represents a hydrogen atom or a straight-chain, branched-chain or cyclic alkyl group or an aralkyl group, which may have a substituent group, and $R_9$ represents an aralkyl or aromatic ring group, both of which may have a substituent group 9 said aromatic ring group may be jointed to the ring II and form together with the nitrogen atom a heterocyclic ring group)].

Examples of the compounds represented by the above general formula are as shown in Table 1.

TABLE 1-continued
| No. | Chemical structural formula |
|---|---|
| 3. | 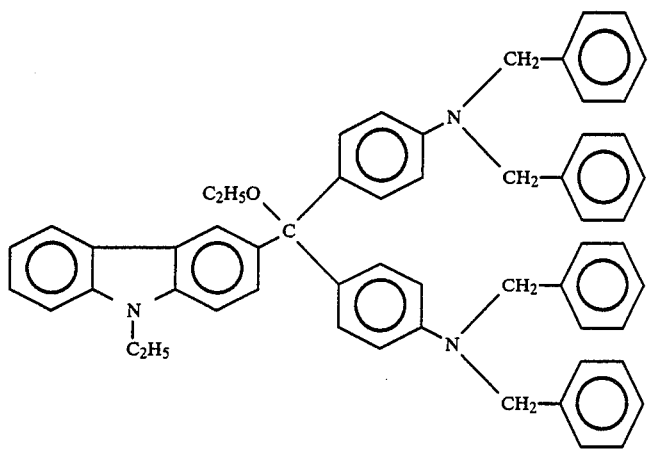 |
| 4. | 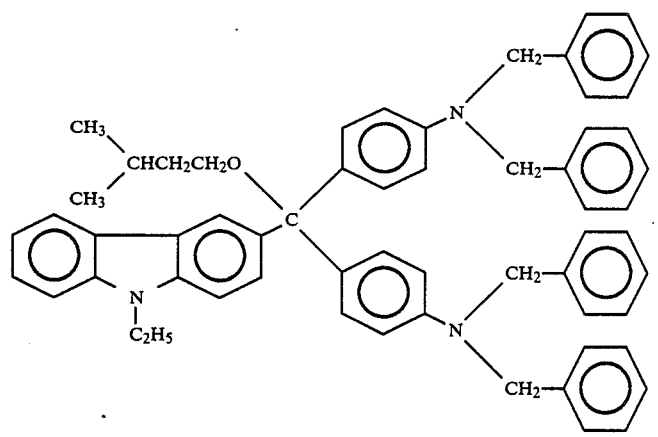 |
| 5. | 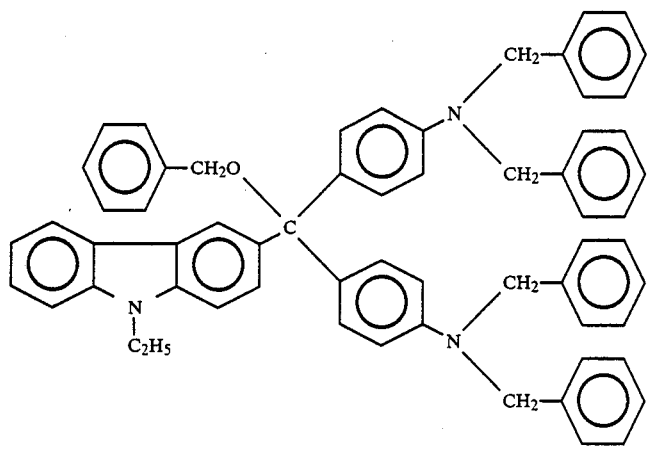 |

TABLE 1-continued
| No. | Chemical structural formula |
|---|---|
| 6. | 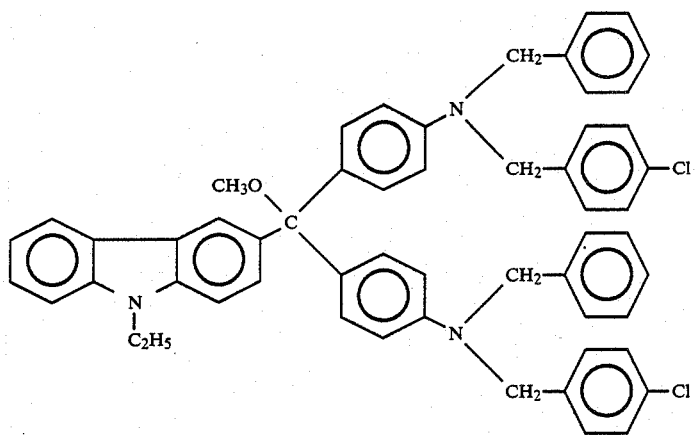 |
| 7. | 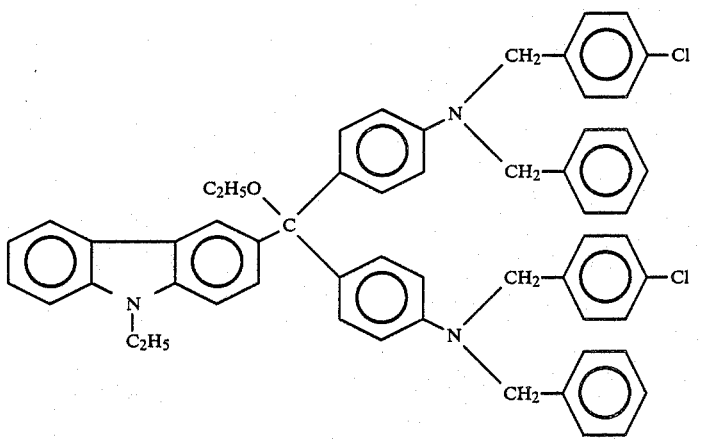 |
| 8. | 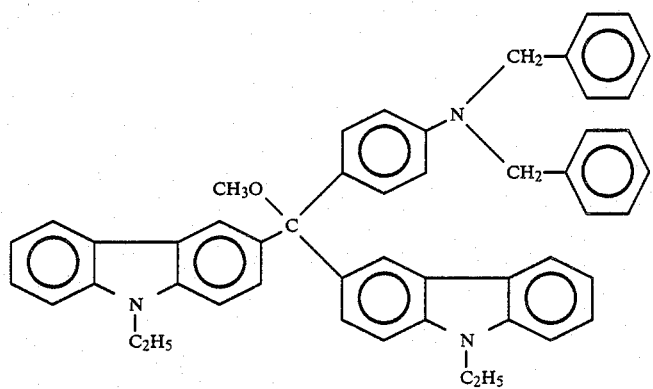 |

TABLE 1-continued
| No. | Chemical structural formula |
| --- | --- |
| 9. | 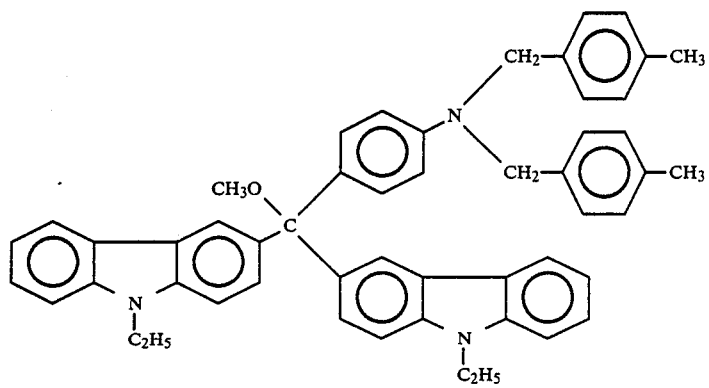 |
| 10. | 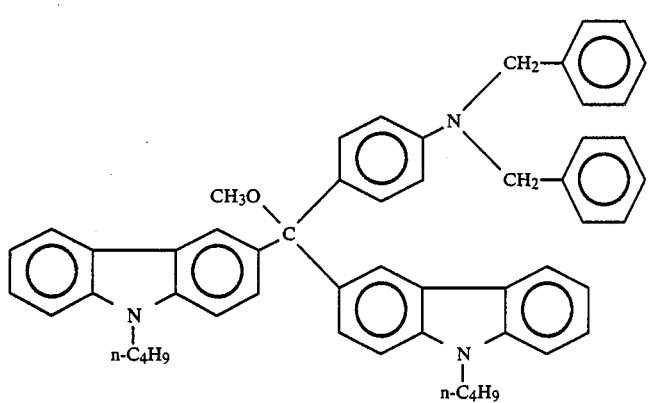 |
| 11. | 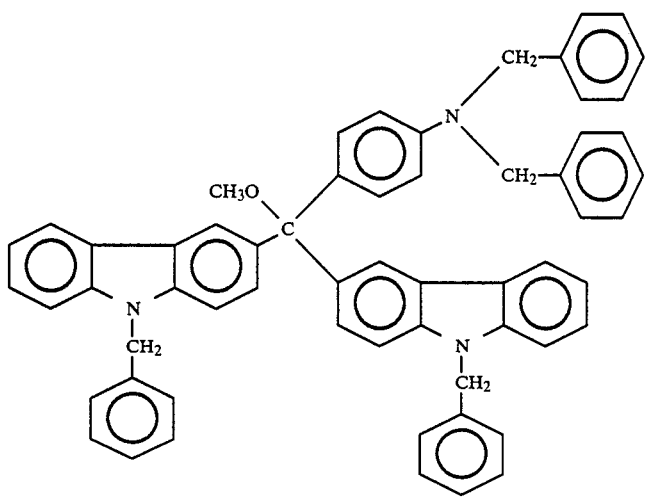 |

TABLE 1-continued
| No. | Chemical structural formula |
|---|---|
| 12. | 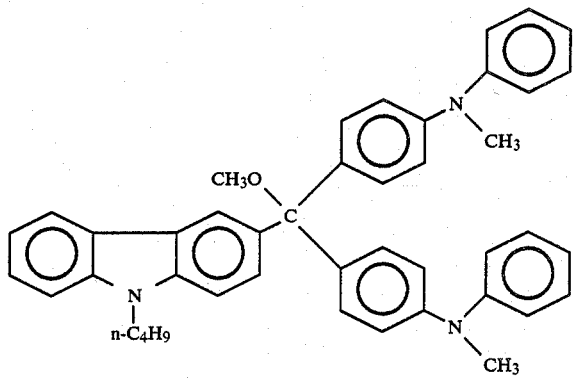 |
| 13. | 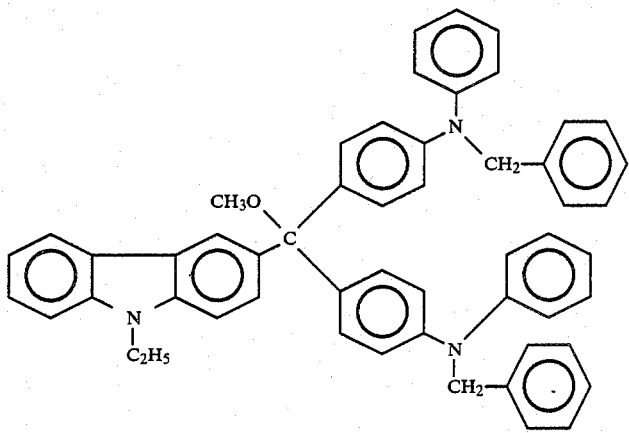 |
| 14. | 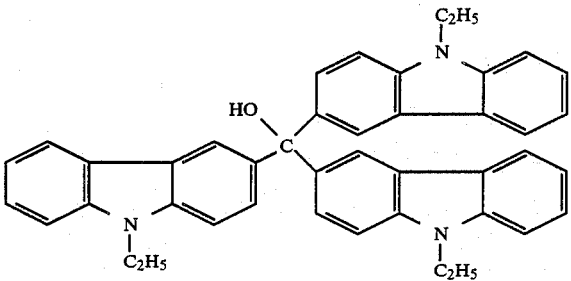 |
| 15. | 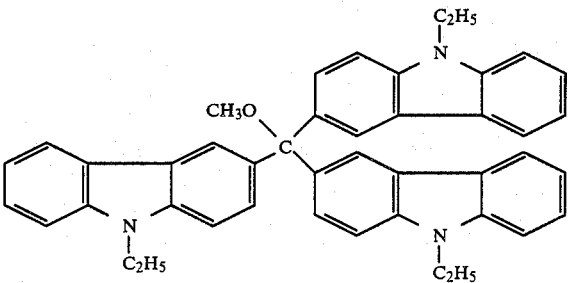 |

TABLE 1-continued

| No. | Chemical structural formula |
|---|---|
| 16. | (structure) |
| 17. | (structure) |
| 18. | (structure) |
| 19. | (structure) |
| 20. | (structure) |

TABLE 1-continued
| No. | Chemical structural formula |
|---|---|
| 21. | 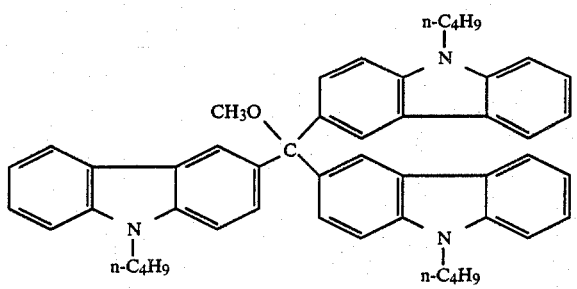 |
| 22. | 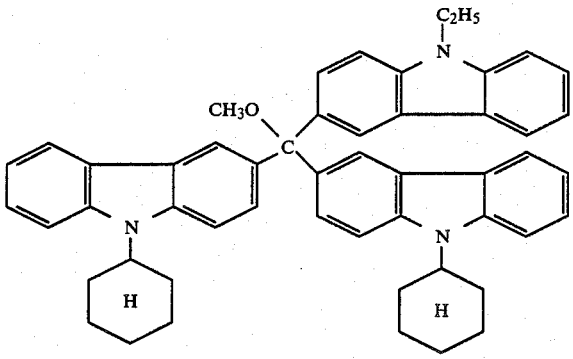 |
| 23. | 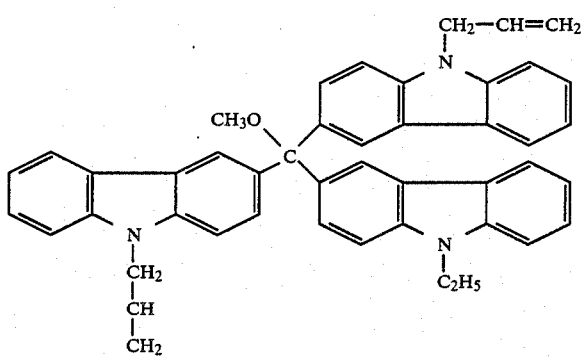 |
| 24. | 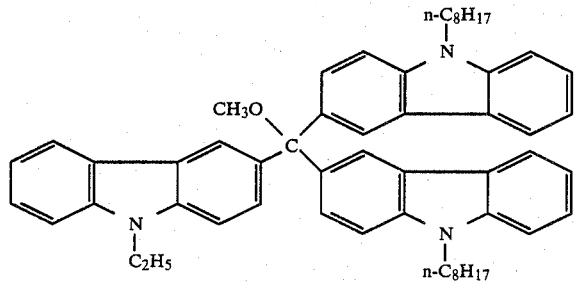 |

TABLE 1-continued
| No. | Chemical structural formula |
|---|---|
| 25. | 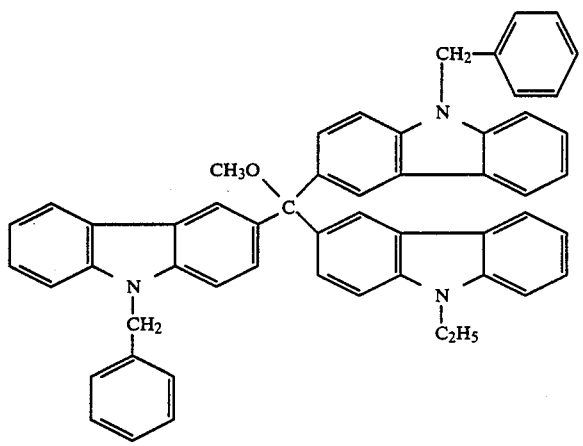 |
| 26. | 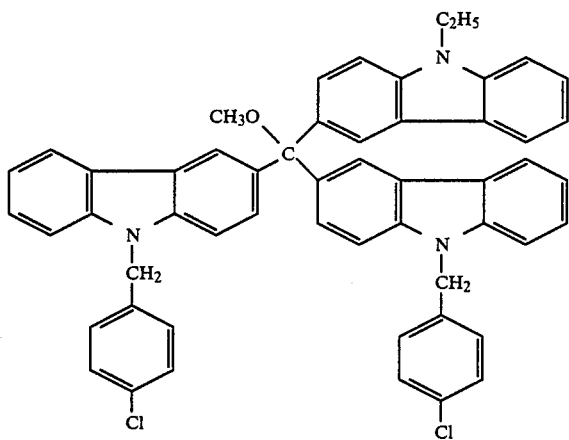 |
| 27. | 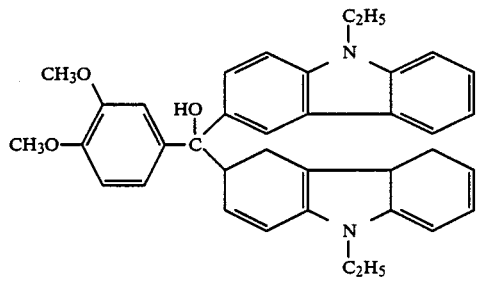 |
| 28. | 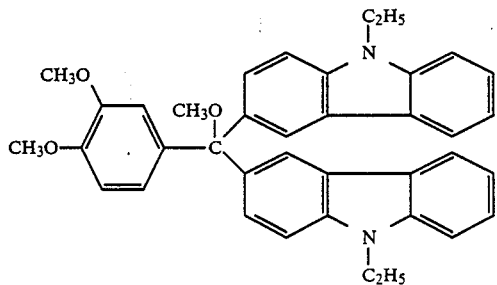 |

TABLE 1-continued
| No. | Chemical structural formula |
|---|---|
| 29. | 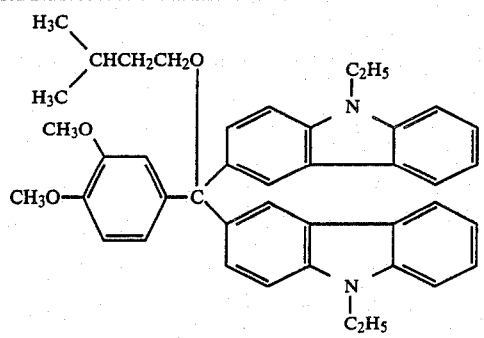 |
| 30. | 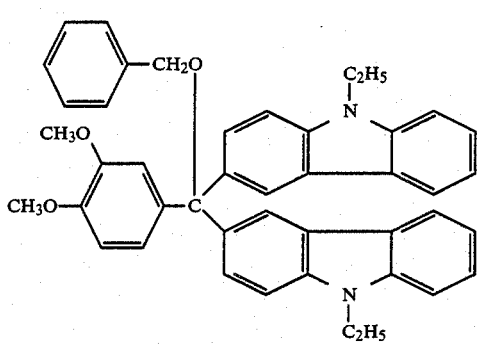 |
| 31. | 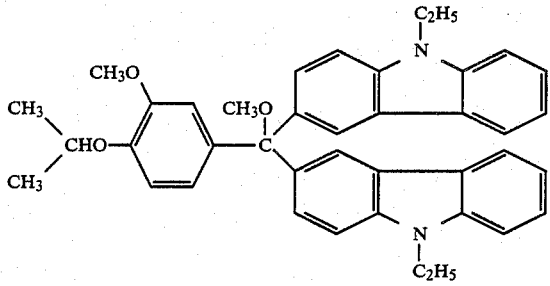 |
| 32. | 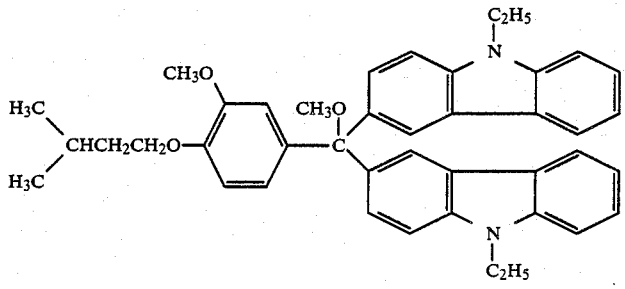 |
| 33. | 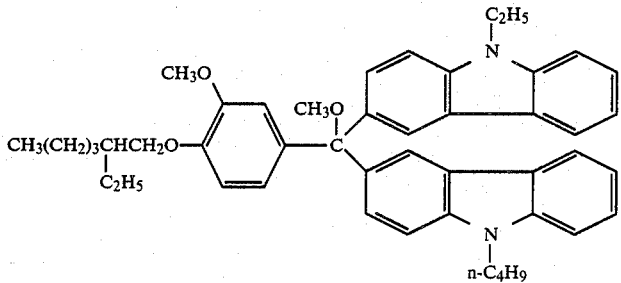 |

TABLE 1-continued

| No. | Chemical structural formula |
|---|---|
| 34. | |
| 35. | |
| 36. | |
| 37. | |

TABLE 1-continued

| No. | Chemical structural formula |
|---|---|
| 38. | 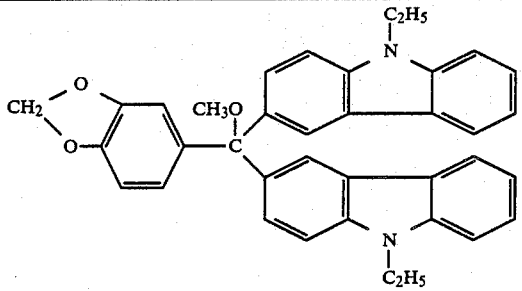 |
| 39. | 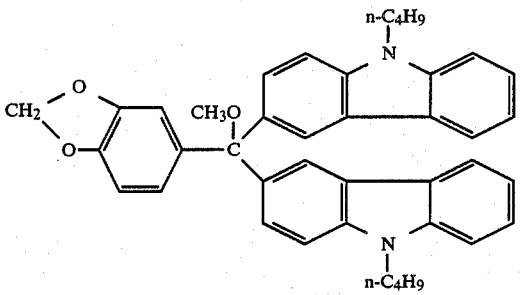 |

These compounds are obtained by condensing 1 mole of an aromatic amine bearing a substituent aldehyde group at the position para with respect to the nitrogen atom (e.g. N,N-dibenzylaminobenzaldehyde and N-n-butylcarbazole-3-carboxyaldehyde) or 3,4-di(ether group)-substituted benzaldehyde (e.g. veratraldehyde and piperonal) with 2 moles of an aromatic amine (e.g. N-benzylcarbazole and N-methyldiphenylamine) under acidic conditions, then oxidizing the resulting tri(amino-substituted aryl)methane or 3,4-di(ether group)-substituted-phenyl-di(amino-substituted)arylmethane with a suitable oxidizing agent to a corresponding dye cation (in blue color), and allowing said dye cation to react with a hydroxide anion or an alkoxide anion to yield the intended product in the form of colorless crystalline solid.

The reason for the molecular design as represented by the above general formula is such that this type of carbinol or carbinol ether shows an acid sensibility suitable for practical purposes as described below.

The present inventors found that a carbinol or a carbinol ether having even one strongly basic aromatic amine, such as N,N-dialkylaniline bonded to the central carbon atom, is too sensitive to an acid to be suitable for practical purposes. For instance, when such a compound is used in a thermosensitive recording sheet, which is one of the important use fields of these compounds, the background of the sheet, which must be white, becomes blue in color due to fogging. Also, if an aqueous solution of such a compound is attempted to be microencapsulated for the purpose of using it in a carbonless pressure-sensitive recording sheet, the aqueous solution turns blue in color upon slight acidification, making the resulting microcapsules useless for practical purposes. Starting from the above experience, the present inventors examined, one by one, various aromatic amines and aryl groups having no amino group and, as a result, found that the compounds of the aforementioned general formula are not excessively sensitive to weak acids but react quickly upon contact with common developers (acid substances) to develop color of high density, suggesting their suitability for the practical purposes. This discovery has led to the present invention.

Furthermore, the inventors have found that among the compounds represented by the general formula (I), especially preferred are those of the general formula (I) wherein $R_4$ is an aromatic ring which is jointed to the ring I to form a carbazole ring together with the nitrogen atom and $R_9$ is an aromatic ring which is jointed to the ring II to form a carbazole ring together with the nitrogen atom, for example, compounds No. 14–26 enumerated hereinbefore, because these compounds are well balanced in the above-mentioned properties. These especially preferred compounds can be obtained as substantially colorless crystalline solid in a high yield by condensing 1 mole of a carbazole derivative having a substituent aldehyde group at 3-position and 2 moles of a carbazole derivative under acidic condition, then oxidizing the resulting tricarbazolylmethane with a suitable oxidizing agent to a corresponding dye cation and thereafter allowing said dye cation to react with a hydroxide anion or an alkoxide anion.

A brief description is given hereunder on the recording materials which will be a major use field for the novel colorless dyes of this invention.

The usual carbonless pressure sensitive recording material consists essentially of an over sheet bearing on the back side a coating layer of microcapsules containing an aqueous solution of electron-donating colorless dye and an under sheet bearing on the front side a coating layer of an electron-accepting developer. Upon application of pressure by hand writing or an impact printer, the microcapsules are ruptured to release the colorless dye which reacts with the developer, thereby producing a colored image.

The thermosensitive recording material comprises a base sheet and, coated thereon, a colorless dye and a developer both in solid form. Upon being imagewise heated by means of a thermal pen, thermal head, laser beam, or electron beam, the colorless dye and the developer in the heated areas react with each other to produce a colored image.

In other types of recording materials such as thermal transfer type and electrothermal type, the mechanism of color formation is the same as described above and the colorless dye of this invention is also useful.

The known colorless lactone dyes such as so-called Crystal Violet Lactone, i.e. 3,3-bis(4-dimethylaminophenyl)-6-dimethylaminophthalide, produces color by the formation of a dye cation through the opening of lactone ring upon contact with an acid developer; whereas the colorless dye of this invention, i.e. a triarylcarbinol or an ether derivative thereof, produces color upon contact with an acid substance by the formation of a dye cation through the elimination of hydroxyl or ether group bonded to the central carbon atom. Therefore, the colorless dye of this invention is quite different from lactone dyes in chemical mechanism of color formation as shown below.

Lactone dyes:

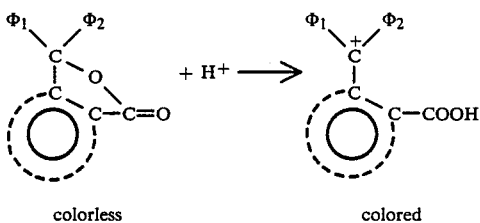

colorless             colored

Triarylcarbinols or ether derivatives thereof:

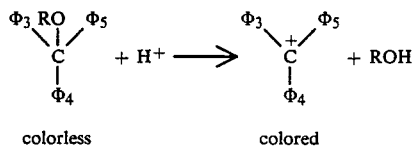

colorless             colored

As examples of acid substances which can be used as developers, mention may be made of clays such as acid clay and activated clay; solid acid of the silica/magnesia type proposed by Japanese Patent Application "Kokai" (Laid-open) No. 15,996/82; phenolic compounds such as 4,4'-isopropylidenediphenol (so-called bisphenol A) and benzyl p-hydroxybenzoate; phenolic resins of the novolac type such as p-octylphenol/formaldehyde resin and p-phenylphenol/formaldehyde resin; polyvalent metal salts of salicylic acid such as zinc 3,5-di-tert-butylsalicylate and zinc 3,5-di-(α-methylbenzyl)salicylate; and compounds which liberate acids upon exposure to light, laser beam, or electron beam.

In the case of colorless dyes of this invention, color is momentarily developed upon contact with any of the acid substances listed above. This is one of the distinct features of the colorless dyes of this invention in contrast to the carbazolylmethane compounds proposed by Japanese Patent Publication No. 16,358/85, which form color very slowly upon contact with an inorganic solid acid and entirely no color when contacted with organic acid substances such as those of phenol type or salicylate type which are most widely used important developers.

The colorless dyes of this invention can be used also in admixture with other colorless dyes to obtain excellent results.

EXAMPLES

Methods for the synthesis of compounds typical of the dyes of the invention for use in recording materials are described in detail below.

SYNTHESIS EXAMPLE 1

A mixture of 1 mole of N-ethylcarbazole-3-aldehyde and 2 moles of N,N-dibenzylaniline was allowed to condense by heating in glacial acetic acid to form 4,4'-di-(N,N-dibenzylaminophenyl)-3-(N-ethylcarbazolyl)methane. A 7.5 g portion of the resulting compound was dissolved in a mixture of 200 ml of dioxane and 200 ml of methanol. To the resulting solution, was added 3.0 g of 2,3-dichloro-5,6-dicyano-1,4-benzoquinone. The mixture was stirred for 2 days at room temperature to form a deep blue solution. After decoloration of the solution with 1 M sodium methoxide solution in methanol, excess methanol was added to the decolored solution. The precipitate was formed was collected by filtration and recrystallized from cyclohexane to yield 3.5 g of 4,4'-di-(N,N-dibenzylaminophenyl)-3-(N-ethylcarbazolyl)carbinol methyl ether (compound No. 2 in Table 1) in the form of colorless crystals melting at 169°–172° C. (decomp.).

Mass analysis (FD method): m/x=782
(Calculated for $C_{56}H_{51}N_3O = 782.038$)

Upon melting by heating a mixture of each a small amount of the above crystals and the crystals of 4,4'-isopropylidenediphenol, a deep blue color appeared instantly. When a solution of the present compound in toluene was added dropwise to silica gel, a deep blue color appeared instantly, whereas when a solution of 4,4'-di-(N,N-dibenzylaminophenyl)-3-(N-ethylcarbazolyl)methane in toluene was added dropwise to silica gel, a blue color appeared after several days.

SYNTHESIS EXAMPLE 2

A mixture of 1 mole of veratraldehyde and 2 moles of N-ethylcarbazole was allowed to condense by dissolving in glacial acetic acid, adding concentrated hydrochloric acid to the solution, and heating the solution. A 5.4 g portion of the resulting 3,4-dimethoxyphenyl-di-(N-ethylcarbazol-3-yl)methane was dissolved in a mixture of 40 ml of dioxane and 40 ml of methanol. Upon addition of 2.4 g of 2,3-dichloro-5,6-dicyano-1,4-benzoquinone to the resulting solution, a blue color appeared instantly. After stirring for 24 hours at room temperature, the blue solution was decolored with 1 M sodium methoxide solution in methanol. Methanol was added in excess to the decolored solution. The colorless precipitate which was formed was collected by filtration and recrystallized from cyclohexane to yield 2.2 g of colorless crystals of 3,4-dimethoxyphenyl-di-(N-ethylcarbazol-3-yl)carbinol methyl ether (compound No. 28 in Table 1) melting at 150° C. (decomp.).

Mass analysis (FD method): m/z=568
(Calculated for $C_{38}H_{36}N_2O_3 = 568.714$)

Upon melting by heating a mixture of each a small amount of the above crystals and the crystals of 4,4'-isopropylidenediphenol, a deep blue color appeared instantly. When a solution of the present compound in toluene was added dropwise to silica gel, a deep blue color appeared instantly, whereas when a solution of 3,4-dimethoxyphenyl-di-(N-ethylcarbazol-3-yl)methane in toluene was added dropwise to silica gel, a blue color appeared after several days.

SYNTHESIS EXAMPLE 3

A mixture of 1 mole of N-ethylcarbazol-3-carboxyaldehyde and 2 moles of N-ethylcarbazole was allowed to condense by dissolving in glacial acetic acid and heating in the presence of hydrochloric acid. A 23.8 g portion of the resulting 3,3',3''-tris-(N-ethylcarbazolyl)methane [colorless needle crystals melting at 207°–210° C. (decomp.)] was dissolved in 150 ml of N,N-dimethylformamide by moderate heating. To the resulting solution, was added dropwise a solution of 10.9 g of 2,3-dichloro-5,6-dicyano-1,4-benzoquinone in 20 ml of N,N-dimethylformamide. The mixture was stirred at 100° C. for 30 minutes to form a deep blue solution. While being kept at 40° C., the solution was decolored by the dropwise addition of 1 N sodium methoxide solution in methanol. The colorless crystals precipitated by the addition of methanol to the said decolored solution were collected by filtration, washed with methanol, dried, and recrystallized from a benzene-n-hexane mixture to yield 22.0 g of colorless crystals melting at 244°–249° C. (decomp.).

Mass analysis (FD method): m/z=625
(Calculated for $C_{44}H_{39}N_3O = 625.812$

The present compound was identical with compound No. 15 in Table 1.

Upon melting, by heating, a mixture of each a small amount of the above crystals and the crystals of 4,4'-isopropylidenediphenol, a deep blue color appeared instantly. When a solution of the present compound in toluene was added dropwise to silica gel, a deep blue color appeared instantly, whereas when a solution of 3,3',3''-tris-(N-ethylcarbazolyl)methane in toluene was added dropwise to silica gel, a blue color appeared after several days.

Other colorless dyes of this invention can be synthesized in substantially the same manner as described above.

EXAMPLE 1

Into 100 g of 1,1-phenylxylylethane, was dissolved 3.1 g of 3,3',3''-tris-(N-ethylcarbazolyl)carbinol methyl ether (compound No. 15 in Table 1) which was a colorless dye of this invention obtained in Synthesis Example 3. The resulting solution was added to 100 g of a 5-% aqueous styrene-maleic anhydride copolymer solution adjusted to pH 4.5. The mixture was treated in a homogenizer to prepare an emulsion (A).

A mixture of 10 g of melamine, 25 g of 37-% formalin and 65 g of water was adjusted to pH 9.0 with sodium hydroxide and heated at 60° C. until a clear aqueous solution (B) containing melamine-formaldehyde early-stage condensate had been obtained.

The solution (B) was added to the emulsion (A) and the mixture was heated with stirring at 60° C. for 3 hours to prepare an aqueous emulsion of microcapsules containing the above aqueous solution of colorless dye enclosed in capsule shells of melamine-formaldehyde resin. The microcapsule emulsion showed no blue color.

A coating composition was prepared by adding 35 g of powdered wheat starch, 30 g of oxidized starch and water to 100 g (dry basis) of the microcapsule emulsion. The solids content of the coating composition was 20 %.

The coating composition was coated on a sheet of wood-free paper, 40 g/m2 in basis weight, at a coverage of 5 g/m2 (dry basis) and dried to obtain an over sheet having white coated surface for use in carbonless pressure sensitive recording paper.

An undersheet was prepared by coating a solid acid of the silica-magnesia type (SS-1, trade name, of Mizusawa Chemical Co.) together with a SBR latex binder on a sheet of wood-free paper at a coverage of 10 g/m2 (dry basis). The over sheet and the under sheet were assembled so that the coated sides of both sheets may face each other. When impression was made under a constant impact pressure by means of typewriter, there appeared instantly letters in beautiful blue color on the under sheet For comparison, an over sheet was prepared in the same manner by using Crystal Violet Lactone in the same amount in terms of mole as those described above in the case of the colorless dye of this invention. Impression was made by using said over sheet and the same under sheet as used above to obtain a blue letter on the under sheet (reference specimen).

The two specimens of under sheets both carrying the blue letters were exposed to direct sunlight. The blue letter on the reference specimen using Crystal Violet Lactone quickly faded, becoming hardly legible after 30 minutes, and completely faded away after 3 hours, whereas the blue letter on the specimen using the colorless dye of this invention hardly faded after 30 minutes of exposure and sufficiently legible after 3 hours.

For further comparison, the following colorless dyes having chemical structures similar to that of the colorless dye of this invention were used in preparing the recording materials.

Reference colorless dye I: di-(4-dimethylaminophenyl)-N-ethylcarbazolylcarbinol methyl ether of the formula

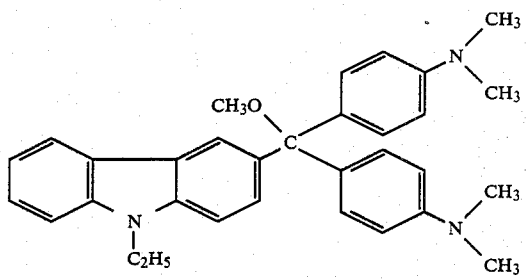

Reference colorless dye II: di-(N-ethylcarbazoly-4-dimethylaminophenylcarbinol methyl ether of the formula

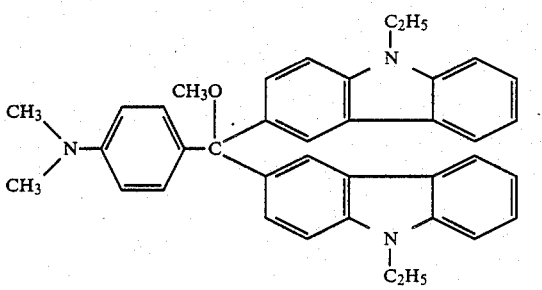

Reference colorless dye III: di-(N-ethylcarbazolyl-4-methoxyphenylcarbinol methyl ether of the formula

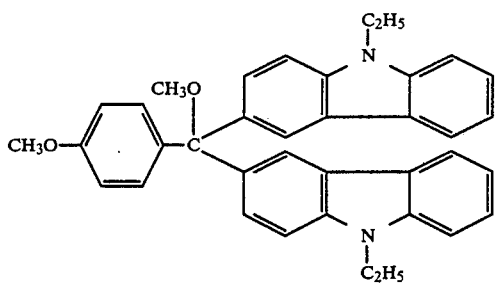

When the reference dyes I and II were used, coloration in deep blue color was observed in the step of microencapsulation, proving the unsuitableness for practical purposes without further test. When the reference dye III was used, although a blue letter was observed on the under sheet, the depth of shade was too low to be useful for practical purposes.

From the above result, it is apparent that the colorless dyes of this invention having the aforementioned chemical structure were desirable for the practical purposes.

EXAMPLE 2

|   | Composition | Parts by weight |
|---|---|---|
| A | Colorless dye No. 34 in Table 1 | 1 |
|   | 5-% aqueous hydroxyethyl-cellulose solution | 6 |
| B | 4,4'-Isopropylidenediphenol | 1 |
|   | 5-% aqueous hydroxyethyl-cellulose solution | 6 |
| C | Stearic acid amide | 1 |
|   | Calcium carbonate | 2 |
|   | 5-% aqueous hydroxyethyl-cellulose solution | 10 |

The compositions A, B and C were independently milled in a ball mill for 2 days and mixed in a ratio of A:B:C=1:5:3. The mixture was coated on a sheet of wood-free paper, 40 g/m² in basis weight, at a coverage of 6 g/m² (dry basis), then dried at 60° C., and finished by passing through a super calender to a Bekk smoothness of 200–300 seconds. The thermosensitive recording paper thus prepared had a white coated surface. A test pattern was impressed by using a facsimile receiver of the thermosensitive type (thin film thermal head) to obtain a blue image of sufficient depth of shade.

A thermosensitive recording sheet was similarly prepared by using the reference colorless dye I or II described in Example 1. The coated surface showed deep blue coloration, proving without further test the unsuitableness for practical purposes. When the reference dye III was used, there was obtained a colored image which was also too low in depth of shade to be sufficiently suitable for practical purposes.

EXAMPLE 3

Microencapsulation was carried out in a manner similar to that in Example 1 using typical colorless dyes of this invention as core materials. The resulting microcapsules were used in preparing the over sheets of carbonless pressure sensitive recording materials. The oversheet and the undersheet were assembled so that the coated surfaces may face each other. The assembly was passed through a super calender to develop color on the under sheet. Each under sheet colored in blue was tested for reflection spectrum in the visible region to determine the wave lengths of absorption maxima ($\lambda_{max}$, nm). The results obtained were as summarized in Table 2.

The developers coated on the under sheet were as follows: ① solid acid of the silica-magnesia type (SS-1, trade name, Mizusawa Chemical Co.), ② p-phenylphenolformaldehyde polycondensation resin, and ③ zinc 3,5-di(α-methylbenzyl)salicylate.

TABLE 2

Wavelength of absorption maximum of the colored image on the under sheet ($\lambda_{max}$, nm)

| Colorless dye No. | ① Solid acid, silica-magnesia type (SS-1, trade name) | ② p-Phenyl-phenol-form-aldehyde polycondensation resin | ③ Zinc 3,5-di-(α-methyl-benzyl)-salicylate |
|---|---|---|---|
| 1 | 600 | 610 | 610 |
| 2 | 600 | 610 | 610 |
| 3 | 600 | 610 | 610 |
| 4 | 600 | 610 | 610 |
| 5 | 600 | 610 | 610 |
| 6 | 595 | 605 | 605 |
| 7 | 595 | 605 | 605 |
| 8 | 585 | 595 | 595 |
| 9 | 605 | 610 | 610 |
| 10 | 585 | 595 | 595 |
| 11 | 585 | 595 | 595 |
| 12 | 610 | 620 | 620 |
| 13 | 605 | 615 | 615 |
| 14 | 600 | 605 | 615 |
| 15 | 600 | 605 | 615 |
| 16 | 600 | 605 | 615 |
| 17 | 600 | 605 | 615 |
| 18 | 600 | 605 | 615 |
| 19 | 600 | 605 | 615 |
| 20 | 600 | 605 | 615 |
| 21 | 600 | 605 | 615 |
| 22 | 600 | 605 | 615 |
| 23 | 600 | 605 | 615 |
| 24 | 600 | 605 | 615 |
| 25 | 600 | 605 | 615 |
| 26 | 600 | 605 | 615 |
| 27 | 610 | 625 | 620 |
| 28 | 610 | 625 | 620 |
| 29 | 610 | 625 | 620 |
| 30 | 610 | 625 | 620 |
| 31 | 610 | 625 | 620 |
| 32 | 610 | 625 | 620 |
| 33 | 610 | 625 | 620 |
| 34 | 610 | 625 | 620 |
| 35 | 610 | 625 | 620 |
| 36 | 610 | 625 | 620 |
| 37 | 610 | 625 | 620 |
| 38 | 600 | 620 | 615 |
| 39 | 600 | 620 | 615 |

All of the colorless dyes used in the present Example produced blue color instantly at $\lambda_{max}$ shown in Table 2. They are, therefore, very useful as primary dyes for use in carbonless pressure sensitive recording materials.

In the case of carbazolylmethane compounds corresponding to intermediates of the synthesis of colorless dyes of this invention, a color of low depth of shade was developed when an inorganic solid acid ① was used as developer, while no color was developed when a phenolic resin ② or zinc salt of a salicylic acid derivative was used.

The colorless dyes of this invention for use in recording materials develop color through a reaction mechanism different from that of known lactone dyes and are triarylcarbinol or triarylcarbinol ether necessarily having a carbazole ring which was selected so as to make the colorless dye practically useful for the recording materials. Being moderate in the sensibility to acids, the present colorless dyes do not discolor nor stain the recording material, yet can develop deep blue color instantly upon contact with any of the common developers to provide recorded images of high depth of shade. Moreover, the recorded image is excellent in fastness, especially in fastness to light and plasticizers. The developed color is substantially the same in hue as that developed by Crystal Violet Lactone which is most popular colorless dye developing blue color. Therefore, the present colorless dye has a practical merit of readily replacing Crystal Violet Lactone.

What is claimed is:

1. A colorless dye for use in recording materials comprising a compound represented by the formula:

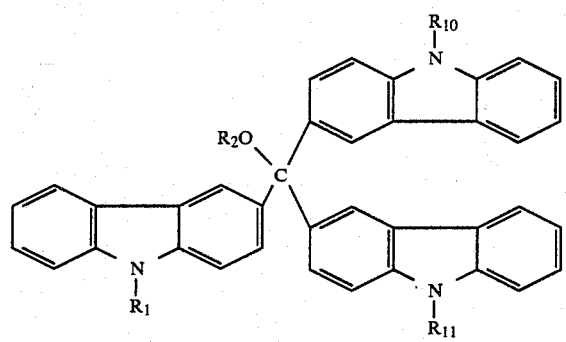

wherein $R_1$ and $R_2$ are independently hydrogen, a straight-chain, branched-chain, or cyclic alkyl group, an alkenyl group, or an aralkyl group which may have a substituent group; $R_{10}$ is hydrogen, a straight-chain, branched-chain, or cyclic alkyl group or an aralkyl group, which may have a substituent group; and $R_{11}$ is hydrogen, a straight-chain, banched-chain, or cyclic alkyl group, an alkenyl group, or an aralkyl group which may have a substituent group.

2. A colorless dye according to claim 1, wherein the compound is represented by the formula:

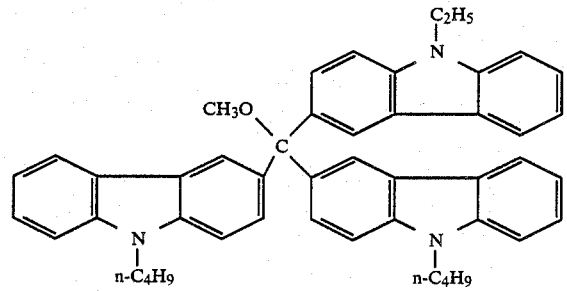

3. A colorless dye according to claim 1, wherein the compound is represented by the formula:

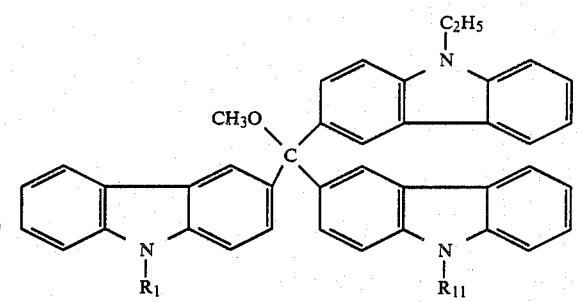

wherein $R_1$ is ethyl, isopropyl, n-butyl, cyclohexyl, allyl,

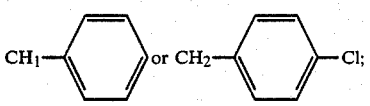

and $R_{11}$ is ethyl, n-butyl, n-octyl, cyclohexyl, or

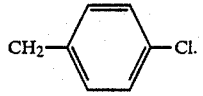

4. A colorless dye according to claim 1 wherein the compound is represented by the formula:

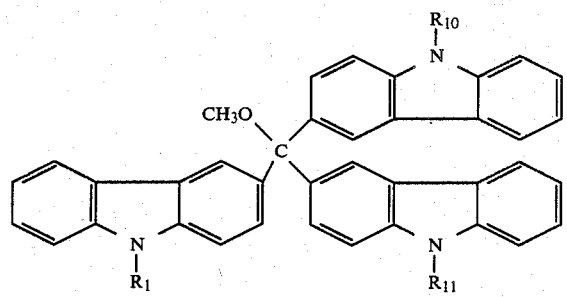

wherein $R_1$ is ethyl isopropyl, n-butyl, cyclohexyl, allyl,

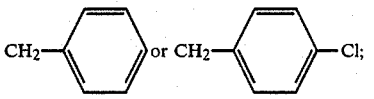

$R_{10}$ is ethyl, isopropyl, n-butyl, n-octyl, allyl or

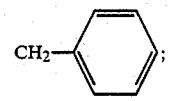

and $R_{11}$ is ethyl, n-butyl, n-octyl, cyclohexyl or

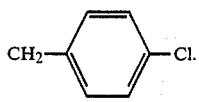

5. A colorless dye according to claim 1, wherein the compound is represented by the formula:

[structure: tri-carbazolyl methanol ether with $R_1$, $R_{10}$, $R_{11}$ on carbazole nitrogens and $OR_2$ on central carbon]

wherein $R_1$ is ethyl, isopropyl, n-butyl, cyclohexyl, allyl,

[structure: $CH_2$-phenyl or $CH_2$-phenyl-Cl];

$R_2$ is hydrogen, methyl, ethyl, pentyl, or

[structure: phenyl-CH];

$R_{10}$ is ethyl, isopropyl, n-butyl, n-octyl, allyl or

[structure: $CH_2$-phenyl];

and $R_{11}$ is ethyl, n-butyl, n-octyl, cyclohexyl, or

[structure: $CH_2$-phenyl-Cl].

* * * * *